(12) United States Patent
Lange et al.

(10) Patent No.: US 8,461,184 B2
(45) Date of Patent: Jun. 11, 2013

(54) SULPHUR CONTAINING PYRAZOLE DERIVATIVES AS SELECTIVE CANNABINOID $CB_1$ RECEPTOR ANTAGONISTS

(75) Inventors: Josephus H. M. Lange, Weesp (NL); Cornelis G. Kruse, Weesp (NL); Bernard J. Vliet Van, Weesp (NL)

(73) Assignee: Solvay Pharmaceuticals B.V., Weesp (NL)

( * ) Notice: Subject to any disclaimer, the term of this patent is extended or adjusted under 35 U.S.C. 154(b) by 294 days.

(21) Appl. No.: 12/844,156

(22) Filed: Jul. 27, 2010

(65) Prior Publication Data

US 2010/0292204 A1    Nov. 18, 2010

Related U.S. Application Data

(62) Division of application No. 11/754,544, filed on May 29, 2007, now Pat. No. 7,786,144.

(60) Provisional application No. 60/809,367, filed on May 31, 2006.

(51) Int. Cl.
 *A61K 31/4155* (2006.01)
 *A61K 31/4453* (2006.01)
 *C07D 231/10* (2006.01)
 *C07D 403/12* (2006.01)

(52) U.S. Cl.
 USPC ........... 514/329; 546/184; 546/192; 546/211; 548/356.1; 548/364.1; 514/317; 514/326; 514/406

(58) Field of Classification Search
 USPC ............ 546/184, 192, 211; 548/356.1, 364.1; 514/315, 317, 326, 329, 406
 See application file for complete search history.

(56) References Cited

U.S. PATENT DOCUMENTS 7,728,018 B2 *  6/2010  Van Loevezijn et al. ...... 514/364
7,786,144 B2 *  8/2010  Lange et al. .................. 514/329

* cited by examiner

*Primary Examiner* — Golam M M Shameem
(74) *Attorney, Agent, or Firm* — Finnegan, Henderson, Farabow, Garrett & Dunner LLP

(57) ABSTRACT

The present invention relates to sulphur containing pyrazole derivatives, and their S-oxidized active metabolites, as selective cannabinoid $CB_1$ receptor antagonists having a high $CB_1$/$CB_2$ receptor subtype selectivity, to methods for the preparation of these compounds, to novel intermediates useful for the synthesis of these pyrazole derivatives, to pharmaceutical compositions comprising one or more of these pyrazole derivatives as active ingredients, as well as to the use of these pharmaceutical compositions for the treatment of psychiatric and neurological disorders. The compounds have the general formula (I)

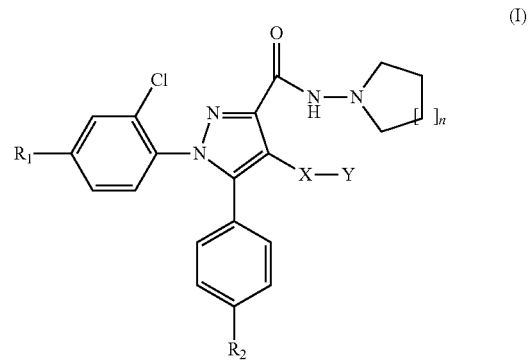

wherein the symbols have the meanings given in the specification.

5 Claims, No Drawings

SULPHUR CONTAINING PYRAZOLE DERIVATIVES AS SELECTIVE CANNABINOID CB₁ RECEPTOR ANTAGONISTS

This is a divisional of application Ser. No. 11/754,544, filed May 29, 2007 now U.S. Pat. No. 7,786,144, and claims the benefit of U.S. Provisional Application No. 60/809,367, filed May 31, 2006, all of which are incorporated herein by reference.

Pyrazole derivatives having CB receptor affinity are known from several patent applications, (including WO 98/43636, WO 98/43635, WO 2005/000820, WO2006/030124, WO 2004/099157, EP 0876350 and US 2006/0100208), and other publications (Lan et al., J. Med. Chem. 1999, 42, 769-776; Francisco et al., J. Med. Chem. 2002, 45, 2708-2719; Katoch-Rouse et al., J. Med. Chem. 2003, 46, 642-645; Meschler et al., Biochem. Pharmacol. 2000, 60, 1315-1323; Matthews et al., J. Labelled Compds. Radiopharm. 1999, 42, 589-596). $CB_1$ receptor antagonists, in particular SR141716A, now known as rimonabant, and their potential therapeutic applications, have been the subject of several reviews (Boyd, S. T. and Fremming, B. A., Ann. Pharmacother. 2005, 39, 684-690; Sorbera, L. A. et al., Drugs Fut. 2005, 30, 128-137; Carai, M. A. M. et al., Life Sc. 2005, 77, 2339-2350; Lange, J. H. M. and Kruse, C. G., Curr, Opin, Drug Discovery Dev. 2004, 7, 498-506, Lange, J. H. M. and Kruse, C. G., Drug Discov. Today 2005, 10, 693-702; Hertzog, D. L., Expert Opin. Ther. Patents 2004, 14, 1435-1452; Smith, R. A. and Fathi, Z., IDrugs 2005, 8, 53-66; Thakur, G. A. et al., Mini-Rev. Med. Chem. 2005, 5, 631-640; Padgett, L. W., Life Sc. 2005, 77, 1767-1798; Muccioli, G. G. et al., Curr. Med. Chem. 2005, 12, 1361-1394, Muccioli, G. G. and Lambert, D. M., Expert Opin. Ther. Patents 2006, 16, 1405-1423; Reggio, P. H., Curr. Pharm. Des. 2003, 9, 1607-1633; Adam, J. et al., Progress in Med. Chem. 2006, 44, 207-329, Eds. King and Lawton, Elsevier, Amsterdam). The abovementioned patent applications and articles disclose a number of $CB_1/CB_2$ receptor subtype selective receptor antagonists. Cannabinoid (CB) receptors are part of the endocannabinoid system, which is involved in neurological, psychiatric, cardiovascular, gastrointestinal, reproductive, and eating disorders as well as in cancer (De Petrocellis, L. et al., Br. J. Pharmacol. 2004, 141, 765-774; Di Marzo, V. et al., Nature Rev. Drug Discov. 2004, 3, 771-784; Lambert, D. M. and Fowler, C. J., J. Med. Chem. 2005, 48, 5059-5087; Vandevoorde, S. and Lambert, D. M., Curr. Pharm. Des. 2005, 11, 2647-2668; Centonze, D. et al., Trends Pharmacol. Sci. 2007, 28, 180-187).

$CB_1$ receptor modulators have several potential therapeutic applications, such as their use as medicaments for treating psychosis, anxiety, depression, attention deficits, memory disorders, cognitive disorders, appetite disorders, obesity, addiction, appetence, drug dependence, neurodegenerative disorders, dementia, dystonia, muscle spasticity, tremor, epilepsy, multiple sclerosis, traumatic brain injury, stroke, Parkinson's disease, Alzheimer's disease, epilepsy, Huntington's disease, Tourette's syndrome, cerebral ischaemia, cerebral apoplexy, craniocerebral trauma, stroke, spinal cord injury, neuroinflammatory disorders, plaque sclerosis, viral encephalitis, demyelinisation related disorders, as well as for the treatment of pain disorders, including neuropathic pain disorders, septic shock, glaucoma, diabetes, cancer, emesis, nausea, gastrointestinal disorders, gastric ulcers, diarrhoea, sexual disorders, impulse control disorders, and cardiovascular disorders.

$CB_2$ receptors occur predominantly in the immune system (spleen, tonsils, immune cells) as well as in microglial cells and astrocytes and have recently also been found in the central nervous system brainstem and cerebellum (Van Sickle et at., Science 2005, 310, 329-332; Ashton et al., Neuroscience Lett. 2006, 396, 113-116).

Potent $CB_1$ receptor modulators having low $CB_2$ receptor affinity (i.e., compounds having a high $CB_1/CB_2$ receptor subtype selectivity) are advantageous compounds as compared to non-selective or less selective cannabinoid receptor modulators as they will be devoid of undesired $CB_2$ receptor mediated side-effects, such as immunologic or inflammatory related side-effects or effects on neuropathic pain perception.

A goal of the present invention was to further develop orally active $CB_1$ receptor antagonists with a high $CB_1/CB_2$ receptor subtype selectivity.

Certain pyrazole derivatives of formula (I), in which X (See below) represents a $CH_2$ group, are known to be $CB_1$ receptor antagonists, Surprisingly, it was found that replacement of this $CH_2$ group by a sulphur atom results in compounds that not only are $CB_1/CB_2$ receptor subtype selective $CB_1$ receptor antagonists, but that are more potent than their non-sulphur containing analogs when tested orally in an in vivo $CB_1$ receptor mediated pharmacological assay. Compounds of the general formula (I) wherein X represents a S=O or a $SO_2$ group can be considered metabolites of the compounds of the general formula (I) wherein X represents a sulphur atom. Such compounds of the general formula (I) wherein X represents a S=O (sulfoxide) or a $SO_2$ (sulfone) group were also surprisingly found to elicit significant $CB_1$ receptor affinities and as a result can be considered active S-oxidized metabolites of the compounds of the general formula (I) wherein X represents a sulphur atom. In general, the formation of active metabolites is known to enhance the potency of therapeutics in vivo. Active metabolites of the general formula (I) wherein X represents a S=O or a $SO_2$ group are part of the present invention. Cytochrome P450 is an important endogenous enzyme which is involved in such metabolic oxidations of alkyl sulfides into the corresponding sulfoxides and sulfones (Denisov et al., Chem. Rev. 2005, 105, 2253-2277; Nnane et al., Eur. J. Drug Metab. Pharmacokin. 2001, 26, 17-24).

The present invention relates to compounds of the general formula (I):

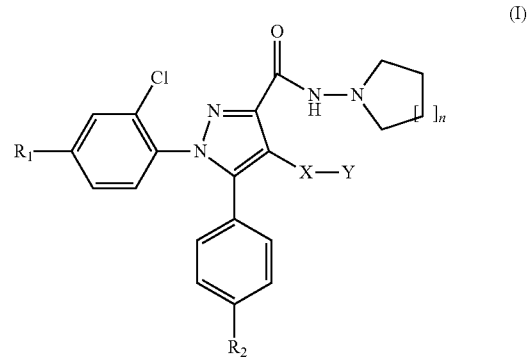

wherein:
$R_1$ represents H, Cl or Br,
$R_2$ represents Cl or Br,
X represents a sulphur atom, a sulfoxide (S=O) or a sulfone ($SO_2$) moiety,
Y represents a methyl or an ethyl group, and
n can have the value 1, 2 or 3,
and tautomers, stereoisomers, prodrugs and N-oxides thereof, and isotopically-labelled compounds of formula (I), as well as pharmacologically acceptable salts, hydrates and solvates of said compounds of formula (I) and its tautomers, stereoisomers, prodrugs, N-oxides or isotopically-labelled analogs.

All sulfoxides within this invention contain a center of chirality. The invention relates to racemates, mixtures of diastereomers, as well as the individual stereoisomers of the compounds having formula (I). The invention also relates to the E isomer, Z isomer and E/Z mixtures of compounds having formula (I).

The invention also relates to compounds of the general formula (I) in which $R_1$ and $R_2$ represent Cl, Y represents a methyl group, X has the meanings as given above, and n represents 1 or 2.

Additionally, the invention relates to the compounds represented by the formula:

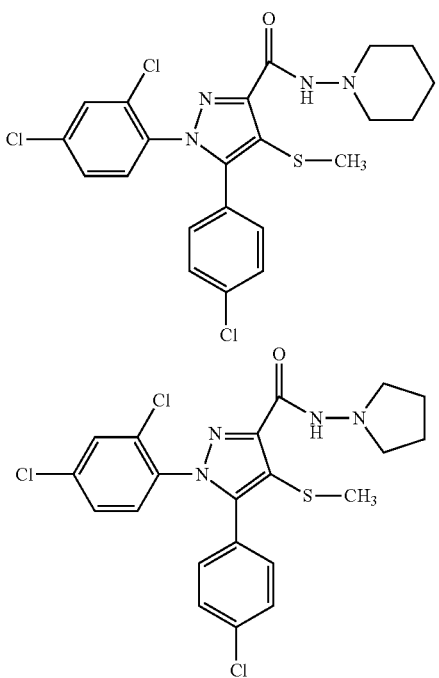

Due to the potent $CB_1$ antagonistic or inverse agonist activity, the compounds according to the invention are suitable for use in the treatment of psychiatric disorders, such as psychosis, anxiety, depression, attention deficits, memory disorders, cognitive disorders, appetite disorders, obesity, in particular juvenile obesity and drug induced obesity, addiction, appetence, drug dependence and neurological disorders, such as neurodegenerative disorders, dementia, dystonia, muscle spasticity, tremor, epilepsy, multiple sclerosis, traumatic brain injury, stroke, Parkinson's disease, Alzheimer's disease, epilepsy, Huntington's disease, Tourette's syndrome, cerebral ischaemia, cerebral apoplexy, cranio-cerebral trauma, stroke, spinal cord injury, neuroinflammatory disorders, plaque sclerosis, viral encephalitis, demyelinisation related disorders, as well as for the treatment of pain disorders, including neuropathic pain disorders, and other diseases involving cannabinoid neurotransmission, including the treatment of septic shock, glaucoma, cancer, diabetes, emesis, nausea, asthma, respiratory diseases, gastrointestinal disorders, gastric ulcers, diarrhoea, sexual disorders, impulse control disorders and cardiovascular disorders.

The cannabinoid receptor modulating activity of the compounds of the invention makes them useful in the treatment of obesity, juvenile obesity and drug induced obesity, for example, when used in combination with lipase inhibitors. Specific examples of compounds which can be used in such combination preparations include, but are not restricted to, the synthetic lipase inhibitor orlistat, lipase inhibitors isolated from micro organisms such as lipstatin (from *Streptomyces toxytricini*), ebelactone B (from *Streptomyces aburaviensis*), synthetic derivatives of these compounds, as well as extracts of plants known to possess lipase inhibitory activity, for instance extracts of *Alpinia officinarum* or compounds isolated from extracts such as 3-methylethergalangin (from *A. officinarum*).

The invention also embraces:
a pharmaceutical composition for treating, for example, a disorder or condition treatable by blocking cannabinoid-CB1 receptors, the composition comprising a compound of formula (I) or a pharmaceutically acceptable salt thereof, and a pharmaceutically acceptable carrier;
a method of treating a disorder or condition treatable by blocking cannabinoid-CB1 receptors, the method comprising administering to a mammal in need of such treatment a compound of formula (I) or a pharmaceutically acceptable salt thereof;
a pharmaceutical composition for treating, for example, a disorder or condition selected from the group of disorders listed herein;
a method of treating a disorder or condition selected from the group of disorders listed herein, the method comprising administering to a mammal in need of such treatment a compound of formula (I) or a pharmaceutically acceptable salt thereof;
a pharmaceutical composition for treating the disorders listed herein, the composition comprising a compound of formula (I) or a pharmaceutically acceptable salt thereof, and
a pharmaceutically acceptable carrier;
a method for treating the disorders listed herein, the method comprising administering to a patient in need of such treatment a compound of formula (I) or a pharmaceutically acceptable salt thereof; and
a method of antagonizing a cannabinoid-CB1 receptor that comprises administering to a subject in need thereof, an effective amount of a compound of formula (I).

The invention also provides for the use of a compound or salt according to formula (I) for the manufacture of a medicament.

The invention further relates to combination therapies wherein a compound of the invention, or a pharmaceutically acceptable salt thereof, or a pharmaceutical composition or formulation comprising a compound of the invention, is administered concurrently or sequentially or as a combined preparation with another therapeutic agent or agents, for treating one or more of the conditions listed. Such other therapeutic agent(s) may be administered prior to, simultaneously with, or following the administration of the compounds of the invention.

The invention also provides compounds, pharmaceutical compositions, kits, and methods for treating the disorders listed herein, the methods comprising administering to a patient in need of such treatment a compound of formula (I) or a pharmaceutically acceptable salt thereof.

The compounds of the invention possess cannabinoid-$CB_1$ antagonistic activity. The antagonizing activity of the compounds of the invention is readily demonstrated, for example, by using one or more of the assays described herein or known in the art.

The invention also provides methods of preparing the compounds of the invention and the intermediates used in those methods.

The compounds of the present invention may contain one or more asymmetric centers and can thus occur as racemates and racemic mixtures, single enantiomers, diastereomeric mixtures, and individual diastereomers.

Depending on the nature of the various substituents, the molecule can have additional asymmetric centers. Each such asymmetric center will independently produce two optical isomers. All of the possible optical isomers and diastereomers, in mixtures and as pure or partially purified compounds, belong to this invention. The present invention comprehends all such isomeric forms of these compounds. Formula (I) shows the structure of the class of compounds without preferred stereochemistry. The independent syntheses of these diastereomers, or their chromatographic separations, may be achieved by methods known in the art by appropriate modification of the methodology disclosed therein. Their absolute stereochemistry may be determined by x-ray crystallography of crystalline products or crystalline intermediates, which are derivatized, if necessary, with a reagent containing an asymmetric center of known absolute configuration. Racemic mixtures of the compounds can be separated into the individual enantiomers by methods well-known in the art, such as the coupling of a racemic mixture of compounds to an enantiomerically pure compound to form a diastereomeric mixture, followed by separation of the individual diastereomers by standard methods, such as fractional crystallization or chromatography. The coupling often consists of the formation of salts using an enantiomerically pure acid or base, for example (−)-di-p-toluoyl-D-tartaric acid and/or (+)-di-p-toluoyl-L-tartaric acid. The diastereomeric derivatives may then be converted to the pure enantiomers by cleavage of the added chiral residue. The racemic mixture of the compounds can also be separated directly by chromatographic methods utilizing chiral stationary phases by methods well-known in the art. Alternatively, any enantiomer of a compound may be obtained by stereoselective synthesis using optically pure starting materials or reagents of known configuration by methods well-known in the art.

Cis and trans isomers of the compound of formula (I), or a pharmaceutically acceptable salt thereof, also belong to the invention, as well as tautomers of the compounds of formula (I) or a pharmaceutically acceptable salt thereof.

Some of the crystalline forms for the compounds may exist as polymorphs and such polymorphs are intended to belong to the invention. In addition, some of the compounds may form solvates with water (i.e., hydrates) or common organic solvents. Such solvates also fall within the scope of this invention. Isotopically-labeled compounds of formula (I) or pharmaceutically acceptable salts thereof, including compounds of formula (I) isotopically-labeled to be detectable by PET or SPECT, also fall within the scope of the invention. The same applies to compounds of formula (I) labeled with [$^{13}$C]—, [$^{14}$C]—, [$^{3}$H]—, [$^{18}$F]—, [$^{125}$I]— or other isotopically enriched atoms, suitable for receptor binding or metabolism studies.

Definitions of Chemical and Other Terms

The term 'alkyl' refers to straight or branched saturated hydrocarbon radicals. 'Alkyl($C_{1-3}$)' for example, means methyl, ethyl, n-propyl or isopropyl, and 'alkyl($C_{1-4}$)' means 'methyl, ethyl, n-propyl, isopropyl, n-butyl, 2-butyl, isobutyl or 2-methyl-n-propyr. The term 'aryl' embraces monocyclic or fused bicyclic aromatic or hetero-aromatic groups, including but not limited to furyl, thienyl, pyrrolyl, oxazolyl, thiazolyl, imidazolyl, imidazo[2,1-b][1,3]thiazolyl, pyrazolyl, isoxazolyl, isothiazolyl, pyridyl, pyridazinyl, pyrimidinyl, pyrazinyl, 1,3,5-triazinyl, phenyl, indazolyl, indolyl, indolizinyl, isoindolyl, benzo[b]furanyl, 1,2,3,4-tetrahydro-naphtyl, 1,2,3,4-tetrahydroisoquinolinyl, indanyl, indenyl, benzo[b]thienyl, 2,3-dihydro-1,4-benzodioxin-5-yl, benzimidazolyl, benzothiazolyl, benzo[1,2,5]thia-diazolyl, purinyl, quinolinyl, isoquinolinyl, phtalazinyl, quinazolinyl, quinoxalinyl, 1,8-naphthyridinyl, naphthyl, pteridinyl or azulenyl. 'Halo' or 'Halogen' means chloro, fluoro, bromo or iodo; 'hetero' as in 'heteroalkyl, heteroaromatic' etc. means containing one or more N, O or S atoms. 'Heteroalkyl' includes alkyl groups with heteroatoms in any position, thus including N-bound O-bound or S-bound alkyl groups. The terms "oxy", "thio" and "carbo" as used herein as part of another group respectively refer to an oxygen atom, a sulphur atom, and a carbonyl (C=O) group, serving as linker between two groups, such as for instance hydroxyl, oxyalkyl, thioalkyl, carboxyalkyl, etc. The term "amino" as used herein alone, or as part of another group, refers to a nitrogen atom that may be either terminal, or a linker between two other groups, wherein the group may be a primary, secondary or tertiary (two hydrogen atoms bonded to the nitrogen atom, one hydrogen atom bonded to the nitrogen atom and no hydrogen atoms bonded to the nitrogen atom, respectively) amine. The terms "sulfinyl" and "sulfonyl" as used herein as part of another group respectively refer to an —SO— or an —SO$_2$— group.

As used herein, unless otherwise noted, the term "leaving group" shall mean a charged or uncharged atom or group that departs during a substitution or displacement reaction. Suitable examples include, but are not limited to, Br, Cl, I, mesylate, tosylate, and the like.

N-oxides of the compounds mentioned above belong to the invention. Tertiary amines may or may not give rise to N-oxide metabolites. The extent to which N-oxidation takes place varies from trace amounts to a near quantitative conversion. N-oxides may be more active than their corresponding tertiary amines, or less active. While N-oxides can easily be reduced to their corresponding tertiary amines by chemical means, in the human body this happens to varying degrees. Some N-oxides undergo nearly quantitative reductive conversion to the corresponding tertiary amines, in other cases conversion is a mere trace reaction, or even completely absent (Bickel, M. H., "*The pharmacology and biochemistry of N-oxides,*" 1969 *Pharmacological Reviews*, 21(4): 325-355).

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value. Throughout the description and the claims of this specification the word "comprise" and variations of the word, such as "comprising" and "comprises," are used and are not intended to exclude other additives, components, integers or steps.

Any compound metabolized in vivo to provide the bioactive agent (i.e., the compound of formula (I)) is a prodrug within the scope and spirit of the application. Prodrugs are therapeutic agents, inactive per se but transformed into one or more active metabolites. Thus, in the methods of treatment of the present invention, the term "administering" shall encompass treating the various disorders described with the compound specifically disclosed, or with a compound not specifically disclosed, but that converts to the specified compound in vivo after administration to the patient. Prodrugs are bioreversible derivatives of drug molecules used to overcome specific barriers to the utility of the parent drug molecule. These barriers include, but are not limited to, solubility, permeability, stability, presystemic metabolism and targeting limitations (Bundgaard, H. ed., *Design of Prodrugs*, Elsevier, 1985; King, F. D. ed., *Medicinal Chemistry: Principles and Practice*, 1994, 215; Stella, J., "Prodrugs as therapeutics," 2004 *Expert Opin. Ther. Patents*, 14(3):277-280; Ettmayer, P. et al., "Lessons learned form marketed and investigational prodrugs," 2004 *J. Med. Chem.*, 47: 2393-2404; Järvinen, T. et al., "Design and Pharmaceutical applications of prodrugs," 733-796 in *Drug Discovery Handbook*, S. C. Gad, ed., 2005, John Wiley & Sons, inc., USA). Prodrugs, i.e., compounds that when administered to humans by any known route are metabolised to compounds having formula (I), belong to the invention. In particular, this relates to compounds with primary or secondary amino or hydroxy groups. Such compounds can be reacted with organic acids to yield compounds having formula (I) wherein an additional group is present that is easily removed after administration, for instance, but not limited to amidine, enamine, a Mannich base, a hydroxyl-methylene derivative, an O-(acyloxymethylene carbamate) derivative, carbamate, ester, amide or enaminone.

The term "composition" as used herein encompasses a product comprising specified ingredients in predetermined amounts or proportions, as well as any product that results, directly or indirectly, from combining specified ingredients in specified amounts. In relation to pharmaceutical compositions, this term encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. The pharmaceutical composition includes enough of the active object compound to produce the desired effect upon the progress or condition of diseases. Accordingly, the pharmaceutical compositions of the present invention encompass any composition made by admixing a compound of the present invention and a pharmaceutically acceptable carrier.

Within the context of this application, the term 'combination preparation' comprises both true combinations, meaning compounds of the invention and other medicaments physically combined in one preparation such as a tablet or injection fluid, as well as 'kit-of-parts', comprising compounds of the invention and a lipase inhibitor in separate dosage forms, together with instructions for use, optionally with further means for facilitating compliance with the administration of the component compounds, e.g. label or drawings. With true combinations, the pharmacotherapy by definition is simultaneous. The contents of 'kit-of-parts', can be administered either simultaneously or at different time intervals. Therapy being either concomitant or sequential will be dependant on the characteristics of the other medicaments used, characteristics like onset and duration of action, plasma levels, clearance, etc., as well as on the disease, its stage, and characteristics of the individual patient.

By "pharmaceutically acceptable" it is meant the carrier, diluent or excipient must be compatible with the other ingredients of the formulation and not deleterious to the recipient thereof.

The affinity of the compounds of the invention for cannabinoid receptors was determined as described below. From the binding affinity measured for a given compound of formula (I), one can estimate a theoretical lowest effective dose. At a concentration of the compound equal to twice the measured $K_i$-value, nearly 100% of the cannabinoid-$CB_1$ receptors likely will be occupied by the compound. Converting that concentration to mg of compound per kg of patient yields a theoretical lowest effective dose, assuming ideal bioavailability. Pharmacokinetic, pharmacodynamic, and other considerations may alter the dose actually administered to a higher or lower value. The dosage expediently administered is 0.001-1000 mg/kg, preferably 0.1-100 mg/kg of patient's bodyweight.

The term "therapeutically effective amount" as used herein refers to an amount of a therapeutic agent to treat or prevent a condition treatable by administrating a composition of the invention. That amount is the amount sufficient to exhibit a detectable therapeutic, preventative or ameliorative response in a tissue system, animal or human. The effect may include, for example, treating or preventing the conditions listed herein. The precise effective amount for a subject will depend upon the subject's size and health, the nature and extent of the condition being treated, recommendations of the treating physician (researcher, veterinarian, medical doctor or other clinician), and the therapeutics, or combination of therapeutics, selected for administration. Thus, it is not useful to specify an exact effective amount in advance.

The term "pharmaceutically acceptable salt" refers to those salts that are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. They can be prepared in situ when finally isolating and purifying the compounds of the invention, or separately by reacting them with pharmaceutically acceptable non-toxic bases or acids, including inorganic or organic bases and inorganic or organic acids.

The term "treatment" as used herein refers to any treatment of a mammalian, preferably human condition or disease, and includes: (1) preventing the disease or condition from occurring in a subject predisposed to the disease, but not yet diagnosed as having it, (2) inhibiting the disease or condition, i.e., arresting its development, (3) relieving the disease or condition, i.e., causing the condition to regress, or (4) stopping the symptoms of the disease.

As used herein, the term "medical therapy" includes prophylactic, diagnostic and therapeutic regimens carried out in vivo or ex vivo on humans or other mammals. The term "subject" as used herein, refers to an animal, preferably a mammal, most preferably a human, who has been the object of treatment, observation or experiment.

EXAMPLES

Example 1

Analytical Methods $^1$H NMR spectra were recorded on a Bruker 400 MHz or a 300 MHz instrument using $CDCl_3$ as solvent with tetramethylsilane as an internal standard. $^{13}$C NMR spectra were recorded on a Bruker instrument (100 MHz) using CDCl$_3$ as solvent. Chemical shifts are given in ppm (δ scale) downfield from tetramethylsilane. Coupling constants (J) are expressed in Hz. Flash chromatography was performed using silica gel 60 (0.040-0.063 mm, Merck). Column chromatography was performed using silica gel 60 (0.063-0.200 mm, Merck). Melting points were recorded on a Büchi B-545 melting point apparatus.

Example 2

General Aspects of Syntheses

The synthesis of compounds having formula (I) is outlined in Scheme 1. The synthesis of the intermediates having formula (II) proceeds analogously to published procedures (Lan, 1999; Francisco, 2002; Katoch-Rouse 2003). The carboxylic acid of general formula (II) wherein $R_1$ and $R_2$ have the abovementioned meaning can be brominated to the corresponding 4-bromo derivative (III) using a brominating agent such as bromine in an inert organic solvent such as dichloromethane. This bromo derivative (III) wherein $R_1$ and $R_2$ have the abovementioned meaning can be treated with a strong base such as n-butyllitium in an inert anhydrous organic solvent such as tetrahydrofuran and subsequently reacted with a sulphur-derived electrophile YSSY wherein Y represents a methyl or ethyl group to afford a compound of general formula (IV) wherein $R_1$, $R_2$ and Y have the abovementioned meaning, $R_4$ is a hydrogen atom and X represents a sulphur atom. This compound of general formula (IV) can be converted to the corresponding ester of general formula (V) wherein $R_1$, $R_2$ and Y have the abovementioned meaning, $R_3$ represents a linear $C_{1-3}$ alkyl group (methyl, ethyl or n-propyl), and X represents a sulphur atom. This ester of general formula (V) can be oxidised with one molar equivalent of an oxidizing reagent such as meta-chloroperbenzoic acid to give the corresponding sulfinyl analogue. Alternatively, reaction of a compound of general formula (V) with two or more molar equivalents of meta-chloroperbenzoic acid can convert the sulfanyl moiety to the corresponding sulfonyl moiety. The ester of general formula (V) wherein $R_1$, $R_2$ and Y have the abovementioned meaning and X represents a sulfoxide or sulfone moiety can be hydrolysed—preferably under acidic conditions—to give the corresponding carboxylic acid (VI). The resulting compound of general formula (VI) can be coupled with an amine in the presence of an activating or coupling reagent to give a compound of general formula (I), wherein $R_1$, $R_2$, Y and n have the abovementioned meaning and X represents a sulfoxide (S=O) moiety or a sulfone (SO$_2$) moiety.

Alternatively, a compound of general formula (IV) wherein $R_1$, $R_2$ and Y have the abovementioned meaning and X represents a sulphur atom can be coupled with an amine in the presence of an activating or coupling reagent to give a compound of general formula (I), wherein $R_1$, $R_2$, Y and n have the abovementioned meaning and X represents a sulphur atom Alternatively, an ester derivative having formula (V) can be reacted in a so-called Weinreb amidation reaction with an amine to give a compound of general formula (I), wherein $R_1$, $R_2$, Y and n have the abovementioned meaning and X represents a sulphur atom or a sulfoxide (S=O) moiety or a sulfone (SO$_2$) moiety. Such Weinreb amidation reactions can be promoted by the use of trimethylaluminum Al(CH$_3$)$_3$ (Levin, et al., *Synth common* 1982, 12, 989-993). Activating and coupling methods of amines to carboxylic acids are well documented (Bodanszky, M. and A. Bodanszky, "*The Practice of Peptide Synthesis*," Springer-Verlag, New York, 1994; Akaji, K. et al., *Tetrahedron Lett.* 1994, 35, 3315-3318; Albericio, F. et al., *Tetrahedron Lett.* 1997, 38, 4853-4856; Montalbetti, C. A. G. N. and V. Falque, *Tetrahedron* 2005, 61, 10827-10852).

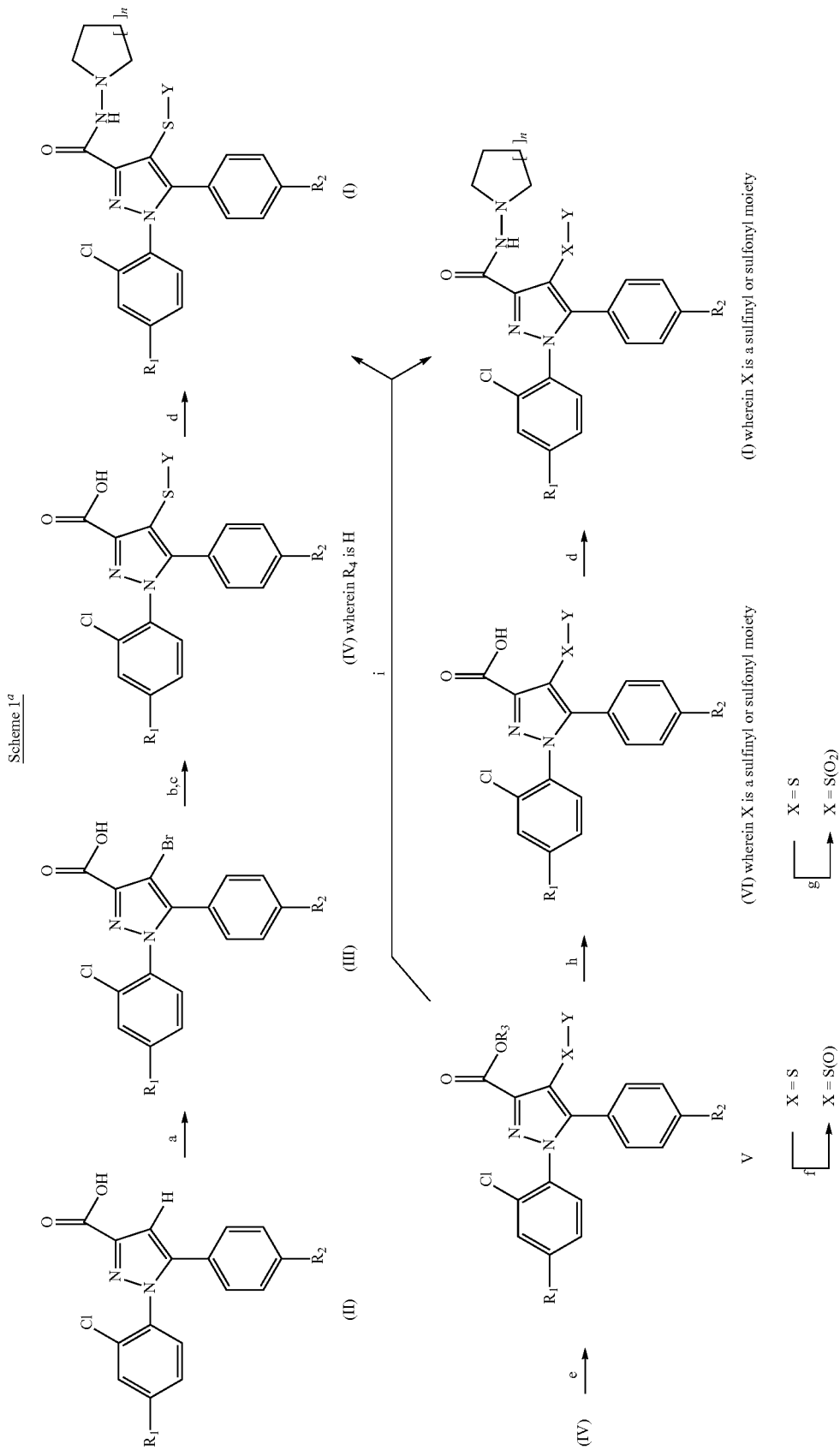
Scheme 1[a]
[a]Reagents and conditions: (a) Br$_2$, CH$_2$Cl$_2$; (b) n-BuLi; THF; (c) R$_3$—OH, acid catalyst or thionylchloride; (d) amine derivative, coupling reagent, dichloromethane, rt; (e) R$_3$—OH, acid catalyst or thionylchloride; (f) 1 equivalent m-CPBA, CH$_2$Cl$_2$, rt; (g) 2 or more equivalents m-CPBA, CH$_2$Cl$_2$, rt; (h) aqueous base; (i) amine, Al(CH$_3$)$_3$ An alternative synthesis of compounds having formula (I) is outlined in Scheme 2. The bromoacetophenone derivative of general formula (VII), wherein $R_2$ has the abovementioned meaning, can be reacted with a compound of general formula NaS—Y to the corresponding 1-aryl-2-(alkylsulfanyl)ethanone derivative (VIII) in an inert organic solvent such as methanol. This 1-aryl-2-(alkylsulfanyl)ethanone derivative (VIII) wherein $R_2$ has the abovementioned meaning can be reacted with an oxalic ester derivative of general formula (IX) in the presence of a base such as sodium alkanoate in an inert anhydrous organic solvent, followed by a reaction with an arylhydrazine (X) or a salt thereof, wherein $R_1$ has the abovementioned meaning to give an ester of general formula (V) wherein $R_1$, $R_2$ and Y have the abovementioned meaning, $R_3$ represents a linear $C_{1-3}$ alkyl group (methyl, ethyl or n-propyl) and X represents a sulphur atom. This ester of general formula (V) can be hydrolyzed under basic conditions, for example with lithium hydroxide, to give the corresponding carboxylic acid of general formula (IV) or its alkali-element (such as lithium, sodium or potassium) salt. This carboxylic acid or carboxylic acid alkali-element salt of general formula (IV) wherein $R_1$, $R_2$ and Y have the abovementioned meaning and X represents a sulphur atom can be coupled with an amine in the presence of an activating or coupling reagent in an inert organic solvent such as dimethylformamide to give a compound of general formula (I), wherein $R_1$, $R_2$, Y and n have the abovementioned meaning and X represents a sulphur atom. This compound of general formula (I), wherein $R_1$, $R_2$, Y and n have the abovementioned meaning and X represents a sulphur atom can be oxidised with one molar equivalent of meta-chloroperbenzoic acid to give the corresponding sulfinyl analogue (X represents a S=O group). Alternatively, reaction of a compound of general formula (I) wherein X represents a sulphur atom with two or more molar equivalents of meta-chloroperbenzoic acid can convert the sulfanyl moiety in (I) to the corresponding sulfonyl moiety.

The selection of the particular synthetic procedures depends on factors known to those skilled in the art, including factors such as the compatibility of functional groups with the reagents used, the possibility to use protecting groups, catalysts, activating and coupling reagents and the ultimate structural features present in the final compound being prepared.

Pharmaceutically acceptable salts may be obtained using standard procedures well known in the art, for example by mixing a compound of the present invention with a suitable acid, for instance an inorganic acid such as hydrochloric acid, or with an organic acid. Hydrates can be obtained using standard procedures well known in the art, for example by crystallization or evaporation from a water-containing (non-anhydrous) organic solvent.

Example 3

Syntheses of Specific Compounds

Compound 1

5-(4-Chlorophenyl)-1-(2,4-dichlorophenyl)-1H-pyrazole-3-carboxylic acid 5-(4-Chlorophenyl)-1-(2,4-dichlorophenyl)-1H-pyrazole-3-carboxylic acid (m.p. 185-187° C.) was obtained from methyl 5-(4-chlorophenyl)-1-(2,4-dichloro-phenyl)-1H-pyrazole-3-carboxylate via ester hydrolysis under basic conditions (methanol, aqueous KOH).

4-Bromo-5-(4-chlorophenyl)-1-(2,4-dichlorophenyl)-1H-pyrazole-3-carboxylic acid

To a magnetically stirred solution of 5-(4-chlorophenyl)-1-(2,4-dichlorophenyl)-1H-pyrazole-3-carboxylic acid (20.0

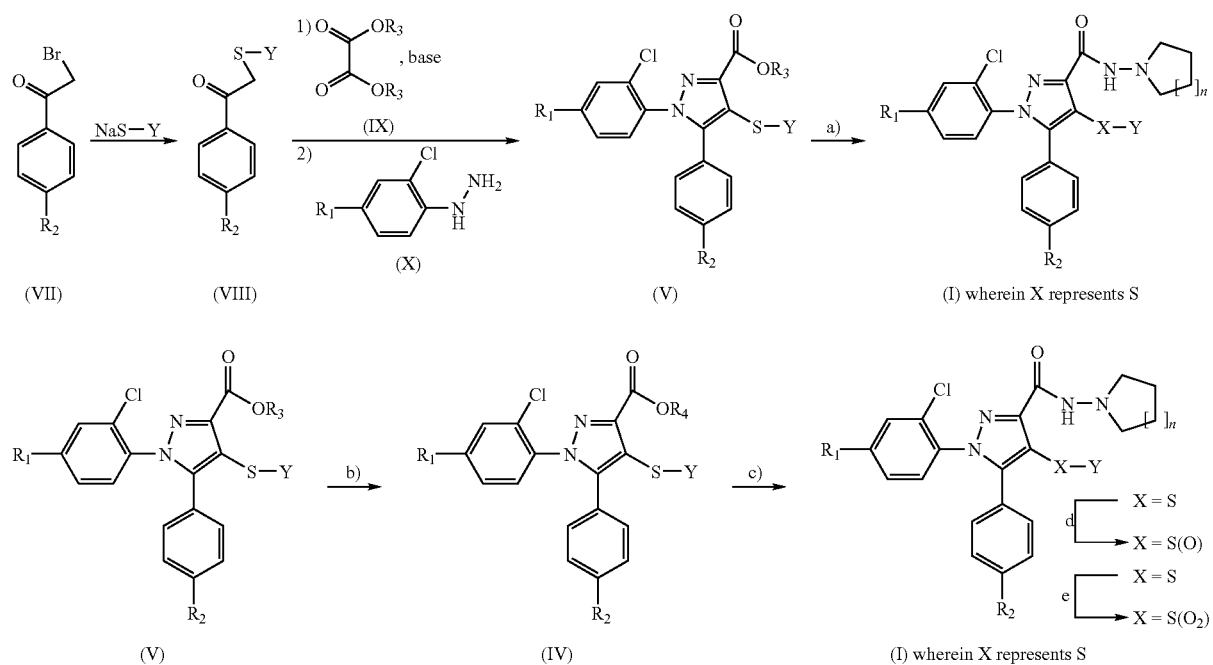

Scheme 2[a]

[a]Reagents and conditions: (a) amine, Al(CH$_3$)$_3$; (b) aqueous base;
(c) amine derivative, coupling reagent, rt; (d) 1 equivalent m-CPBA, CH$_2$Cl$_2$, rt;
(e) 2 or more equivalents m-CPBA, CH$_2$Cl$_2$, rt.

g, 54.5 mmol) in dichloromethane (400 ml) was slowly added bromine (5.62 ml, 109 mmol) and the resulting mixture was reacted for 16 hours at room temperature. Diethyl ether (400 ml) and excess aqueous saturated NaHCO$_3$ solution were successively added. The organic layer was separated, twice washed with aqueous saturated NaHCO$_3$ solution and subsequently washed with brine, dried over MgSO$_4$, filtered and concentrated to give 4-bromo-5-(4-chlorophenyl)-1-(2,4-dichlorophenyl)-1H-pyrazole-3-carboxylic acid (19.77 gram, 81% yield). Melting point: 222-224° C.

5-(4-Chlorophenyl)-1-(2,4-dichlorophenyl)-4-methylsulfanyl-1H-pyrazole-3-carboxylic acid To a magnetically stirred solution of 4-bromo-5-(4-chlorophenyl)-1-(2,4-dichlorophenyl)-1H-pyrazole-3-carboxylic acid (5.00 g, 11.2 mmol) in anhydrous tetrahydrofuran (THF) (250 ml) was added n-butyllithium (15/5 ml, 1.6 M solution, 25.2 mmol) and the resulting solution was stirred for 15 minutes under N$_2$ at −78° C. A solution of dimethyl disulfide (CH$_3$S)$_2$ (3.16 g, 33.6 mmol) in anhydrous THF (20 ml) was added by syringe and the resulting solution was stirred at −78° C. overnight. The reaction mixture was quenched with excess water and the resulting solution was extracted with diethyl ether. The diethyl ether layer was washed with water, dried over MgSO$_4$, filtered and concentrated to give crude 5-(4-chlorophenyl)-1-(2,4-dichlorophenyl)-4-methylsulfanyl-1H-pyrazole-3-carboxylic acid which was further purified using flash chromatography (eluant:dichloromethane/methanol=95/5 (v/v)) followed by another flash chromatographic purification (eluant:dichloromethane/ethanol=95/5 (v/v)) to give 5-(4-chlorophenyl)-1-(2,4-dichlorophenyl)-4-methylsulfanyl-1H-pyrazole-3-carboxylic acid (2.75 g) which was immediately converted in the next reaction step.

5-(4-Chlorophenyl)-1-(2,4-dichlorophenyl)-4-methylsulfanyl-N-(piperidin-1-yl)-1H-pyrazole-3-carboxamide compound 1

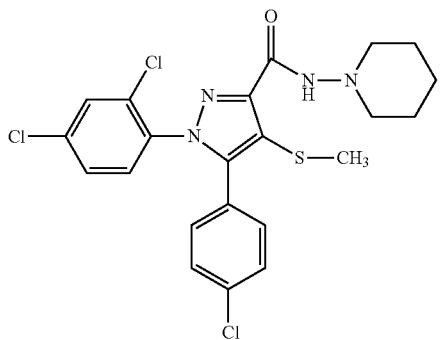

To a magnetically stirred solution of 5-(4-chlorophenyl)-1-(2,4-dichlorophenyl)-4-methylsulfanyl-1H-pyrazole-3-carboxylic acid (4.69 g, 11.3 mmol) in dichloromethane (100 ml) was successively added 7-aza-1-hydroxybenzotriazole (HOAt) (2.2 g, 16.0 mmol), (1-(3-dimethylaminopropyl)-3-ethylcarbodiimide hydrochloride (EDCl) (3.1 g, 16.1 mmol) and 1-aminopiperidine (1.6 gram, 16.0 mmol). After stirring for 16 h, the resulting mixture was successively washed with water (3×), dried over Na$_2$SO$_4$, filtered and concentrated to give a crude solid. This crude solid was further purified by flash chromatography (silica gel, EtOAc/heptane=22178 (v/v)) and trituration with n-heptane/methanol to give 5-(4-chlorophenyl)-1-(2,4-dichlorophenyl)-4-methylsulfanyl-N-(piperidin-1-yl)-1H-pyrazole-3-carboxamide: compound 1 (0.55 gram, 10% yield). Melting point: 172.4-174.5° C. $^1$H-NMR (CDCl$_3$, 400 MHz) δ 1.41-1.49 (m, 2H), 1.72-1.81 (m, 4H), 2.40 (s, 3H), 2.83-2.95 (m, 4H), 7.15 (br d, J=8 Hz, 2H), 7.28-7.35 (m, 4H), 7.42 (br d, J=2 Hz, 1H), 7.94 (br s, 1H). $^{13}$C-NMR (CDCl$_3$, 100 MHz) δ 20.03, 23.32, 25.29, 57.02, 113.66, 126.20, 127.99, 128.74, 130.36, 130.48, 131.24, 132.85, 135.59, 135.64, 136.41, 147.08, 147.30, 158.62.

Compound 2

1-(4-Chlorophenyl)-2-(methylsulfanyl)ethanone

To a magnetically stirred solution of bromo-4-chloro-acetophenone (16.8 g, 72 mmol) in methanol (200 ml) was added NaSCH$_3$ (5.23 g, 72 mmol) to give an exothermic reaction. The resulting mixture was reacted for 2 hours at room temperature, concentrated and suspended in dichloromethane (150 ml) and washed with water, dried over MgSO$_4$, filtered and concentrated to give 1-(4-chlorophenyl)-2-(methylsulfanyl)ethanone (5.1 gram). $^1$H-NMR (CDCl$_3$, 400 MHz) δ 2.13 (s, 3H), 3.72 (s, 2H), 7.44 (br d, J=8 Hz, 2H), 7.92 (br d, J=8 Hz, 2H).

Ethyl 5-(4-chlorophenyl)-1-(2,4-dichlorophenyl)-4-methylsulfanyl-1H-pyrazole-3-carboxylate Sodium metal (2 gram, 87 mmol) was dissolved in ethanol (80 ml). The resulting solution was added to a magnetically stirred solution of diethyl oxalate (6 gram, 41 mmol) and 1-(4-chlorophenyl)-2-(methylsulfanyl)ethanone (8.0 g, 40 mmol). The resulting mixture was reacted for 20 hours at room temperature and subsequently poured into aqueous hydrochloric acid (200 ml, 1 N). The resulting mixture was extracted twice with methyl-tert-butyl ether (MTBE) (200 ml), dried over MgSO$_4$, filtered and concentrated. The resulting residue was dissolved in acetic acid (200 ml), 2,4-dichlorophenylhydrazine.HCl (8.6 gram, 40 mmol) was added and the resulting mixture was heated at 60° C. for 3 hours. The reaction mixture was allowed to attain room temperature, concentrated to approximately 50 ml and poured into water (200 ml), followed by extraction with MTBE (3 portions of 150 ml). The combined organic layers were washed with 5% aqueous NaHCO$_3$, dried over MgSO$_4$, filtered and concentrated. Further purification using column chromatography (silica gel; eluant: heptane/ethylacetate=90/10 (v/v)) gave ethyl 5-(4-chlorophenyl)-1-(2,4-dichlorophenyl)-4-methylsulfanyl-1H-pyrazole-3-carboxylate (4.9 gram, 27% yield). R$_f$~0.4 (heptane/ethylacetate=90/10 (v/v)). $^1$H-NMR (CDCl$_3$, 300 MHz) δ 1.44 (t, J=7 Hz, 3H), 2.32 (s, 3H), 4.46 (q, J=7, 2H), 7.10-7.45 (m, 7H).

Lithium 5-(4-chlorophenyl)-1-(2,4-dichlorophenyl)-4-methylsulfanyl-1H-pyrazole-3-carboxylate To a magnetically stirred solution of ethyl 5-(4-chlorophenyl)-1-(2,4-dichlorophenyl)-4-methylsulfanyl-1H-pyrazole-3-carboxylate (4.9 g, 11 mmol) in tetrahydrofuran (100 ml) was added LiOH.H$_2$O (0.47 gram, 11 mmol) and the resulting mixture was reacted for 20 hours at 35° C. and subsequently concentrated in vacuo. The obtained crude lithium 5-(4-chlorophenyl)-1-(2,4-dichlorophenyl)-4-methylsulfanyl-1H-pyrazole-3-carboxylate was used in the next step.

5-(4-Chlorophenyl)-1-(2,4-dichlorophenyl)-4-methylsulfanyl-N-(pyrrolidin-1-yl)-1H-pyrazole-3-carboxamide (compound 2)

compound 2

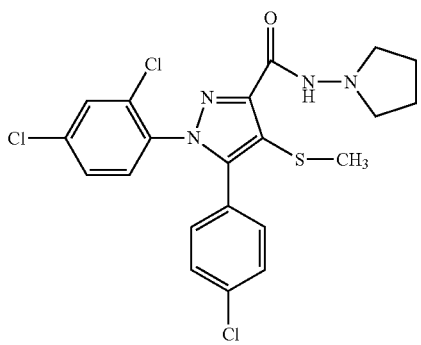

To a magnetically stirred solution of lithium 5-(4-chlorophenyl)-1-(2,4-dichlorophenyl)-4-methylsulfanyl-1H-pyrazole-3-carboxylate (1.2 gram, 3 mmol maximally) in dimethylformamide (35 ml) was successively added O-benzotriazol-1-yl-N,N,N',N'-tetramethyluronium tetrafluoroborate (TBTU) (1.25 g, 3.9 mmol), triethylamine (1.3 ml) and 1-aminopyrrolidine hydrochloride (0.410 gram, 3.35 mmol). After stirring for 18 h at 50° C. the resulting mixture was allowed to attain room temperature and concentrated in vacuo. The remaining residue was triturated with water and successively further purified by flash chromatography (silica gel, EtOAc/heptane=20/80 (v/v)) to give 5-(4-chlorophenyl)-1-(2,4-dichlorophenyl)-4-methyl-sulfanyl-N-(pyrrolidin-1-yl)-1H-pyrazole-3-carboxamide: compound 2 (0.78 gram, 54% yield). $^1$H-NMR (CDCl$_3$, 400 MHz) δ 1.88-1.96 (m, 4H), 2.39 (s, 3H), 3.02-3.08 (m, 4H), 7.15 (br d, J=8 Hz, 2H), 7.29-7.33 (m, 4H), 7.42 (br s, 1H), 7.98 (br s, 1H).

5-(4-Chlorophenyl)-1-(2,4-dichlorophenyl)-4-methylsulfanyl-N-(azepan-1-yl)-1H-pyrazole-3-carboxamide (compound 3)

compound 3

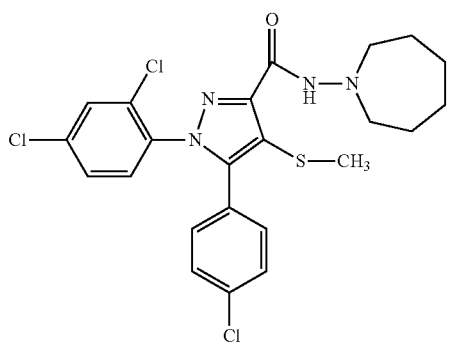

Compound 3 was prepared analogously as described for compound 2 hereinabove from crude lithium 5-(4-chlorophenyl)-1-(2,4-dichlorophenyl)-4-methylsulfanyl-1H-pyrazole-3-carboxylate, azepan-1-ylamine, TBTU and Et$_3$N in DMF in 52% yield.

$^1$H-NMR (CDCl$_3$, 400 MHz) δ 1.64-1.68 (m, 4H), 1.72-1.79 (m, 4H), 2.38 (s, 3H), 3.18-3.22 (m, 4H), 7.15 (br d, J=8 Hz, 2H), 7.29-7.33 (m, 4H), 7.42 (br t, J~2 Hz, 1H), 8.43 (br s, 1H). $^{13}$C-NMR (CDCl$_3$, 100 MHz) δ 20.17, 26.30, 26.99, 58.10, 113.31, 126.26, 127.96, 128.75, 130.36, 130.49, 131.23, 132.86, 135.62, 135.65, 136.36, 147.26, 147.31, 158.87.

5-(4-Chlorophenyl)-1-(2,4-dichlorophenyl)-4-methylsulfonyl-N-(piperidin-1-yl)-1H-pyrazole-3-carboxamide (compound 4)

To a magnetically stirred solution of 5-(4-chlorophenyl)-1-(2,4-dichlorophenyl)-4-methylsulfanyl-N-(piperidin-1-yl)-1H-pyrazole-3-carboxamide (0.70 gram, 1.41 mmol) was added m-CPBA (2.2 gram of a 70% aqueous solution, 9 mmol). The resulting mixture was reacted for 70 hours at room temperature and subsequently poured into water (25 ml). The resulting mixture was extracted with dichloromethane (25 ml). The organic layer was separated and dried over MgSO$_4$, filtered and concentrated. Column chromatography (silica gel, dichloromethane/methanol=95/5 (v/v)) gave 5-(4-chlorophenyl)-1-(2,4-dichlorophenyl)-4-methylsulfonyl-N-(piperidin-1-yl)-1H-pyrazole-3-carboxamide (380 mg, 51% yield, compound 4).

$^1$H-NMR (CDCl$_3$, 400 MHz) δ 1.70-2.10 (m, 6H), 2.47-2.63 (m, 2H), 3.31 (s, 3H), 3.55-3.62 (m, 1H), 3.82-3.90 (m, 1H), 7.12 (br d, J=8 Hz, 2H), 7.31-7.36 (m, 4H), 7.42 (d, J=2, 1H), 10.80 (br s, 1H).

compound 4

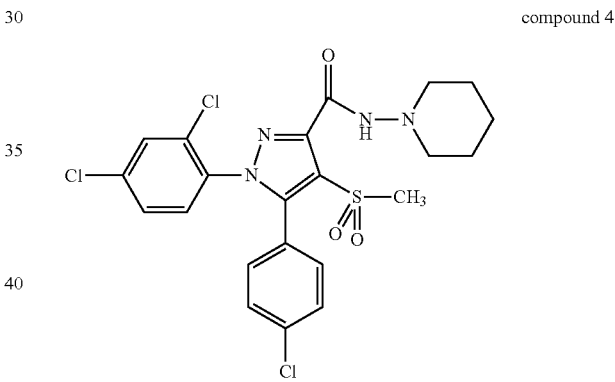

5-(4-Chlorophenyl)-1-(2,4-dichlorophenyl)-4-methylsulfinyl-N-(piperidin-1-yl)-1H-pyrazole-3-carboxamide (compound 5)

compound 5

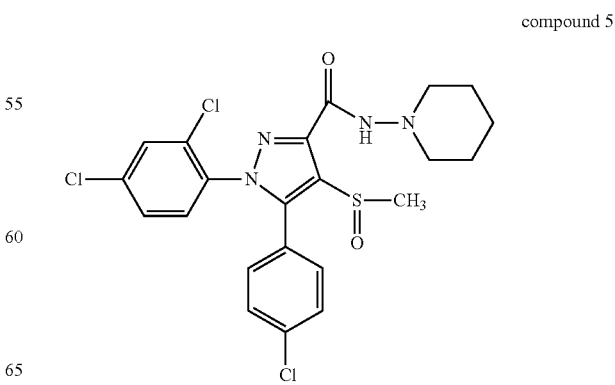

To a magnetically stirred solution of 5-(4-chlorophenyl)-1-(2,4-dichlorophenyl)-4-methylsulfanyl-N-(piperidin-1-yl)-1H-pyrazole-3-carboxamide (0.70 gram, 1.41 mmol) was added m-chloro-perbenzoic acid (m-CPBA) (0.50 gram of a 70% aqueous solution, 2.0 mmol). The resulting mixture was reacted for 20 hours at room temperature and subsequently poured into water (25 ml). The resulting mixture was extracted with dichloromethane (25 ml). The organic layer was separated and dried over $MgSO_4$, filtered and concentrated. Column chromatography (silica gel, dichloromethane/methanol=95/5 (v/v)) gave 5-(4-chlorophenyl)-1-(2,4-dichlorophenyl)-4-methyl-sulfinyl-N-(piperidin-1-yl)-1H-pyrazole-3-carboxamide (150 mg, 21% yield) (compound 5).

$^1$H-NMR ($CDCl_3$, 400 MHz) δ 1.41-1.49 (m, 2H), 1.72-1.81 (m, 4H), 2.84-2.96 (m, 4H), 3.11 (s, 3H), 7.15 (br d, J=8 Hz, 2H), 7.27-7.32 (m, 4H), 7.43 (br s, 1H), 8.70 (br s, 1H). $^{13}$C-NMR ($CDCl_3$, 100 MHz) δ 23.28, 25.22, 41.84, 56.97, 122.91, 124.67, 128.03, 128.66, 130.41, 130.63, 131.60, 133.01, 134.54, 136.51, 136.98, 144.62, 144.85, 157.60.

Example 4

Pharmacological Methods

In vitro affinity for human cannabinoid-$CB_1$ receptors.

The affinity of the compounds of the invention for cannabinoid $CB_1$ receptors can be determined using membrane preparations of Chinese hamster ovary (CHO) cells in which the human cannabinoid $CB_1$ receptor is stably transfected in conjunction with [$^3$H]CP-55,940 as radioligand. After incubation of a freshly prepared cell membrane preparation with the [$^3$H]-ligand, with or without addition of compounds of the invention, separation of bound and free ligand is performed by filtration over glassfiber filters. Radioactivity on the filter is measured by liquid scintillation counting.

In vitro affinity for human cannabinoid-$CB_2$ receptors.

The affinity of the compounds of the invention for cannabinoid $CB_2$ receptors can be determined using membrane preparations of Chinese hamster ovary (CHO) cells in which the human cannabinoid $CB_2$ receptor is stably transfected in conjunction with [$^3$H]CP-55,940 as radioligand. After incubation of a freshly prepared cell membrane preparation with the [$^3$H]-ligand, with or without addition of compounds of the invention, separation of bound and free ligand is performed by filtration over glassfiber filters. Radioactivity on the filter was measured by liquid scintillation counting.

In vitro cannabinoid-$CB_1$ receptor antagonism.

In vitro $CB_1$ receptor antagonism can be assessed with the human $CB_1$ receptor cloned in Chinese hamster ovary (CHO) cells. CHO cells are grown in a Dulbecco's Modified Eagle's medium (DMEM) culture medium, supplemented with 10% heat-inactivated fetal calf serum. Medium is aspirated and replaced by DMEM, without fetal calf serum, but containing [$^3$H]-arachidonic acid and incubated overnight in a cell culture stove (5% $CO_2$/95% air; 37° C.; water-saturated atmosphere). During this period [$^3$H]-arachidonic acid is incorporated in membrane phospholipids. On the test day, medium is aspirated and cells are washed three times using 0.5 ml DMEM, containing 0.2% bovine serum albumin (BSA). Stimulation of the $CB_1$ receptor by WIN 55,212-2 lead to activation of $PLA_2$ followed by release of [$^3$H]-arachidonic acid into the medium. This WIN 55,212-2-induced release is concentration-dependently antagonized by $CB_1$ receptor antagonists.

CP-55,940 Induced Hypotension in the rat.

Male normotensive rats (225-300 g; Harlan, Horst, The Netherlands) were anaesthetized with pentobarbital (80 mg/kg i.p). Blood pressure was measured, via a cannula inserted into the left carotid artery, by means of a Spectramed DTX-plus pressure transducer (Spectramed B. V., Bilthoven, The Netherlands). After amplification by a Nihon Kohden Carrier Amplifier (Type AP-621 G; Nihon Kohden B. V., Amsterdam, The Netherlands), the blood pressure signal was registered on a personal computer (Compaq Deskpro 386s), by means of a Po—Ne-Mah data-acquisition program (Po—Ne-Mah Inc., Storrs, USA). Heart rate was derived from the pulsatile pressure signal. All compounds were administered orally as a microsuspension in 1% methylcellulose 30 minutes before induction of the anesthesia which was 60 minutes prior to administration of the $CB_1$ receptor agonist CP-55,940. The injection volume was 10 ml/kg. After haemodynamic stabilization the $CB_1$ receptor agonist CP-55,940 (0.1 mg/kg i.v.) was administered and the hypotensive effect established.

Example 5

Pharmacological Test Results

Affinity data for human cannabinoid $CB_1$ and $CB_2$ receptors (mean results of at least three independent experiments, performed according to the protocols given above) of rimonabant and compounds 1-5 are given in the table below. These data illustrate the impact on $CB_1$ and $CB_2$ receptor affinities, $CB_{1/2}$ receptor selectivity ratios as well as their in vivo potency after oral administration achieved by the structural modification that forms the basis of the present invention, and also illustrate the $CB_1$ receptor affinities of the S-oxidized compounds 4 and 5.

TABLE 1

$CB_1$ and $CB_2$ receptor affinities and in vivo activity in CB receptor-mediated rat model of rimonabant and compounds 1-3 of this invention and $CB_1$ receptor affinities for the S-oxidized compounds 4 and 5; nd = not determined.

| compound | X | Y | n | $hCB_1$ $K_i$(nM) | $hCB_2$ $K_i$(nM) | $CB_1/CB_2$ ratio | Blood pressure (rat) $ED_{50}$ (mg/kg, p.o.) |
|---|---|---|---|---|---|---|---|
| rimonabant | $CH_2$ | H | 2 | 25 | 1580 | 63 | 3.2 |
| Comp. 1 | S | $CH_3$ | 2 | 10 | 668 | 67 | 1.5 |
| Comp. 2 | S | $CH_3$ | 1 | <10 | 340 | >34 | 1.9 |
| Comp. 3 | S | $CH_3$ | 3 | 20 | 500 | 25 | 3.1 |
| Comp. 4 | S=O | $CH_3$ | 2 | 13 | nd | — | nd |
| Comp. 5 | $SO_2$ | $CH_3$ | 2 | 250 | nd | — | nd |

Example 6

Pharmaceutical Preparations

For clinical use, compounds of formula (I) are formulated into a pharmaceutical compositions that are important and novel embodiments of the invention because they contain the compounds, more particularly specific compounds disclosed herein. Types of pharmaceutical compositions that may be used include, but are not limited to, tablets, chewable tablets, capsules (including microcapsules), solutions, parenteral solutions, ointments (creams and gels), suppositories, suspensions, and other types disclosed herein or apparent to a person skilled in the art from the specification and general knowledge in the art. The compositions are used for oral, intravenous, subcutaneous, tracheal, bronchial, intranasal, pulmonary, transdermal, buccal, rectal, parenteral or other ways to administer. The pharmaceutical formulation contains at least one compound of formula (I) in admixture with a pharmaceutically acceptable adjuvant, diluent and/or carrier. The total amount of active ingredients suitably is in the range of from about 0.1% (w/w) to about 95% (w/w) of the formulation, suitably from 0.5% to 50% (w/w) and preferably from 1% to 25% (w/w). The compounds of the invention can be brought into forms suitable for administration by means of usual processes using auxiliary substances such as liquid or solid, powdered ingredients, such as the pharmaceutically customary liquid or solid fillers and extenders, solvents, emulsifiers, lubricants, flavorings, colorings and/or buffer substances. Frequently used auxiliary substances include magnesium carbonate, titanium dioxide, lactose, saccharose, sorbitol, mannitol and other sugars or sugar alcohols, talc, lactoprotein, gelatin, starch, amylopectin, cellulose and its derivatives, animal and vegetable oils such as fish liver oil, sunflower, groundnut or sesame oil, polyethylene glycol and solvents such as, for example, sterile water and mono- or polyhydric alcohols such as glycerol, as well as with disintegrating agents and lubricating agents such as magnesium stearate, calcium stearate, sodium stearyl fumarate and polyethylene glycol waxes. The mixture may then be processed into granules or pressed into tablets.

The active ingredients may be separately premixed with the other non-active ingredients, before being mixed to form a formulation. The active ingredients may also be mixed with each other, before being mixed with the non-active ingredients to form a formulation.

Soft gelatine capsules may be prepared with capsules containing a mixture of the active ingredients of the invention, vegetable oil, fat, or other suitable vehicle for soft gelatine capsules. Hard gelatine capsules may contain granules of the active ingredients. Hard gelatine capsules may also contain the active ingredients together with solid powdered ingredients such as lactose, saccharose, sorbitol, mannitol, potato starch, corn starch, amylopectin, cellulose derivatives or gelatine. Dosage units for rectal administration may be prepared (i) in the form of suppositories that contain the active substance mixed with a neutral fat base; (ii) in the form of a gelatine rectal capsule that contains the active substance in a mixture with a vegetable oil, paraffin oil or other suitable vehicle for gelatine rectal capsules; (iii) in the form of a ready-made micro enema; or (iv) in the form of a dry micro enema formulation to be reconstituted in a suitable solvent just prior to administration.

Liquid preparations may be prepared in the form of syrups, elixirs, concentrated drops or suspensions, e.g. solutions or suspensions containing the active ingredients and the remainder consisting, for example, of sugar or sugar alcohols and a mixture of ethanol, water, glycerol, propylene glycol and polyethylene glycol. If desired, such liquid preparations may contain coloring agents, flavoring agents, preservatives, saccharine and carboxymethyl cellulose or other thickening agents. Liquid preparations may also be prepared in the form of a dry powder, reconstituted with a suitable solvent prior to use. Solutions for parenteral administration may be prepared as a solution of a formulation of the invention in a pharmaceutically acceptable solvent. These solutions may also contain stabilizing ingredients, preservatives and/or buffering ingredients. Solutions for parenteral administration may also be prepared as a dry preparation, reconstituted with a suitable solvent before use.

Also provided according to the present invention are formulations and 'kits of parts' comprising one or more containers filled with one or more of the ingredients of a pharmaceutical composition of the invention, for use in medical therapy. Associated with such container(s) can be various written materials such as instructions for use, or a notice in the form prescribed by a governmental agency regulating the manufacture, use or sale of pharmaceuticals products, which notice reflects approval by the agency of manufacture, use, or sale for human or veterinary administration. The use of formulations of the present invention in the manufacture of medicaments for use in treating a condition in which antagonism of cannabinoid-$CB_1$ receptors is required or desired, and methods of medical treatment or comprising the administration of a therapeutically effective total amount of at least one compound of formula (I), either as such or in the case of prodrugs, after administration, to a patient suffering from, or susceptible to, a condition in which antagonism of cannabinoid-$CB_1$ receptors is required or desired.

We claim:

1. A method for treating at least one disorder in a patient in need thereof, wherein said at least one disorder is chosen from psychosis, anxiety, depression, attention deficits, memory disorders, cognitive disorders, appetite disorders, obesity, addiction, appetence, drug dependence, dementia, dystonia, muscle spasticity, tremor, epilepsy, multiple sclerosis, traumatic brain injury, stroke, Parkinson's disease, Alzheimer's disease, epilepsy, Huntington's disease, Tourette's syndrome, cerebral ischaemia, cerebral apoplexy, craniocerebral trauma, stroke, spinal cord injury, neuroinflammatory disorders, plaque sclerosis, vital encephalitis, demyelinisation related disorders, neuropathic pain disorders, septic shock, glaucoma, diabetes, emesis, nausea, asthma, respiratory diseases, gastrointestinal disorders, gastric, ulcers, diarrhoea, and sexual disorders, said method comprising administering to the patient a pharmacologically effective amount of at least one compound of formula (I),

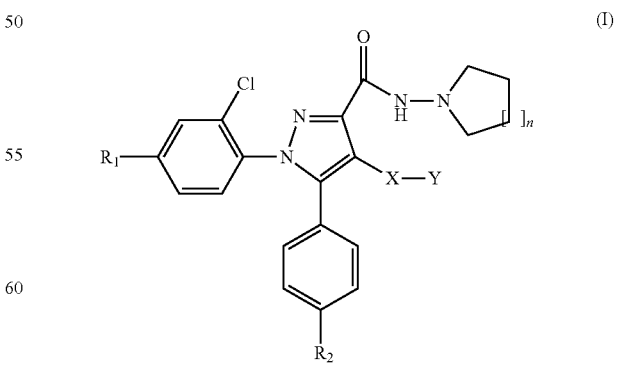

wherein:
$R_1$ represents H, Cl or Br,
$R_2$ represents Cl or Br,

X represents a sulphur atom, a sulfoxide (S=O) or a sulfone (SO$_2$) moiety,

Y represents a methyl or an ethyl group, and n can have the value 1, 2 or 3, or a tautomer, stereoisomer, prodrug or N-oxide thereof, or a pharmacologically acceptable salt of said compounds of formula (I), or a tautomer, stereoisomer, or N-oxide of any of the foregoing.

2. The method as claimed in claim 1, wherein the at least one disorder is chosen from appetite disorders and obesity.

3. The method as claimed in claim 2, wherein the at least one disorder is obesity and is chosen from juvenile obesity and drug induced obesity.

4. The method as claimed in claim 2, further comprising administration of at least one lipase inhibitor.

5. The method as claimed in claim 4, wherein said lipase inhibitor is orlistat or lipstatin.

* * * * *